United States Patent
Gijlers

(10) Patent No.: US 8,585,970 B2
(45) Date of Patent: Nov. 19, 2013

(54) FLOW THROUGH CARTRIDGE FOR SELECTING AN ANALYTE ONLINE WITH HIGH PERFORMANCE LIQUID CHROMATOGRAPHY

(75) Inventor: Hermannus Geert Gijlers, Emmen (NL)

(73) Assignee: Spark Holland B.V., Emmen (NL)

( * ) Notice: Subject to any disclaimer, the term of this patent is extended or adjusted under 35 U.S.C. 154(b) by 572 days.

(21) Appl. No.: 12/801,443

(22) Filed: Jun. 9, 2010

(65) Prior Publication Data

US 2011/0008224 A1    Jan. 13, 2011

Related U.S. Application Data

(60) Provisional application No. 61/213,765, filed on Jul. 13, 2009.

(30) Foreign Application Priority Data

Jul. 13, 2009 (EP) .................................. 09165343

(51) Int. Cl.
G01N 30/60 (2006.01)

(52) U.S. Cl.
USPC ............... 422/69; 422/70; 422/527; 422/554; 210/198.2; 210/282; 73/23.39; 73/61.53; 96/101; 96/108; 264/349

(58) Field of Classification Search
USPC ........... 422/69, 70, 527, 554; 210/198.2, 282; 96/101, 108; 73/61.53, 23.39; 264/349
See application file for complete search history.

(56) References Cited

U.S. PATENT DOCUMENTS

| | | | |
|---|---|---|---|
| 3,254,771 A * | 6/1966 | Sicard | 210/266 |
| 5,180,491 A * | 1/1993 | Polasky | 210/282 |
| 5,866,004 A | 2/1999 | Houck et al. | |
| 6,294,627 B1 | 9/2001 | Worm et al. | |
| 6,877,363 B2 * | 4/2005 | Sattler et al. | 73/61.53 |
| 7,431,900 B2 * | 10/2008 | Hill et al. | 422/305 |
| 2002/0108860 A1 | 8/2002 | Staats | |
| 2005/0092685 A1 | 5/2005 | Hilhorst et al. | |

FOREIGN PATENT DOCUMENTS

| | | |
|---|---|---|
| EP | 0 446 970 A3 | 9/1991 |
| EP | 1 329 705 A2 | 7/2003 |
| EP | 1 159 597 B1 | 8/2007 |
| WO | WO 00/54023 A1 | 9/2000 |

OTHER PUBLICATIONS

"The Glass Transition" http://www.pslc.ws/macrog/tg.htm.*

(Continued)

*Primary Examiner* — Jan Ludlow
(74) *Attorney, Agent, or Firm* — Oliff & Berridge, PLC

(57) ABSTRACT

A flow through cartridge for solid phase extraction of an analyte from a liquid has a cartridge body bounding a passage for retaining a sorbent. The passage extends from a first end face to a second end face, opposite the first end face of the cartridge body. The cartridge body is composed of a core of a first material extending around the passage and sealing rings of a second material, extending around an axis of the passage at the first and second end faces. Surface portions of the sealing rings constituting surface portions of the first and second end faces. The first material is stronger and stiffer than the second material.

15 Claims, 9 Drawing Sheets

(56) References Cited

OTHER PUBLICATIONS

"The Glass Transition" http://www.pslc.ws/macrog/tg.htm[Dec. 7, 2012].*

Extended European Search Report dated Dec. 4, 2009 issued in EP 09165343.6.
Koster et al., "Recent Developments in On-line SPE for HPLC and LC-MS in Bioanalysis,"*Guide LC-MS*, Dec. 2001, pp. 1-3.

* cited by examiner

FLOW THROUGH CARTRIDGE FOR SELECTING AN ANALYTE ONLINE WITH HIGH PERFORMANCE LIQUID CHROMATOGRAPHY

This is a Non-Provisional Application that claims the benefit of U.S. Provisional Application No. 61/213,765 filed Jul. 13, 2009 and European Application No. 09165343.6 filed Jul. 13, 2009. The disclosure of the prior applications is hereby incorporated by reference herein in its entirety.

FIELD AND BACKGROUND OF THE INVENTION

The invention relates to a flow through cartridge for selecting an analyte online with high performance liquid chromatography.

One example for selecting an analyte for detection using high performance liquid chromatography (also known as high pressure liquid chromatography) is solid phase extraction (SPE). SPE uses the affinity of a substance or substances in a liquid (the mobile phase) for a solid (the stationary phase) along which the liquid is passed to separate the substance or substances from the remainder of the sample. The result is that either the substance or substances separated out are retained on the stationary phase. The portion that passes through the stationary phase is collected or discarded, depending on whether it contains the desired analytes or an undesired remainder. If the desired analytes have been retained on the stationary phase, they can then be removed from the stationary phase for collection in an additional step, in which the stationary phase is rinsed with an appropriate eluent, optionally after rinsing to remove substances that have been retained but are not part of the analyte that is subject of further analysis. Conversely, the liquid that has passed along the solid can be analyzed in a next step.

SPE may for instance be carried out as follows:

a) conditioning a sorbent in a cartridge, a liquid suitable for conditioning being passed through the cartridge;

b) applying a sample that contains the analyte to the sorbent, a mobile phase liquid which contains the sample being passed through the cartridge;

c) washing the sorbent, a wash liquid being passed through the cartridge; and d) eluting the analyte from the sorbent, an elution liquid being passed through the cartridge.

Step a) serves to wet the surface of the sorbent to create the stationary phase that absorbs the analyte. In step b) the substance to be tested, the analyte, is applied to the sorbent and, at least to a useful extent, selectively absorbed by the sorbent. In step c) the sorbent is washed so that constituents which could interfere with detection of the analyte are removed. In step d) the analyte is eluted from the sorbent so that it can be detected in a following step, for example by gas chromatographic analysis (GC) or by means of high performance (or pressure) liquid chromatography (HPLC).

Already for quite some time, in particular for automation of bioanalytical assays, especially in the pharmaceutical industry, SPE is more and more carried out in direct communication with HPLC or Mass Spectrometry (MS) downstream of the SPE (usually referred to as "online" or "on-line" with the SPE). Total automation, high precision and high sensitivity are among the most favoured features of online SPE. An example of online SPE and HPLC is described in applicant's European patent 1 159 597 and in *Recent Developments in On-line SPE for HPLC and LC-MS in Bioanalysis*; Emile Koster and Bert Ooms, Guide to LC-MS, December 2001, pp 1-3.

Modern HPLC systems work at high pressures, and therefore are able to use very small particle sizes in the columns (<2 μm). It is known to apply pressures in such "Ultra High Performance (or Pressure) Liquid Chromatography" systems (UHPLCs) of up to 100 MPa.

The cartridge is typically constituted by a body through which a passage extends from one side of the cartridge to an opposite side of the cartridge, packing material and sieves. To manufacture the cartridge at low costs, the body is injection moulded, usually from Polyvinylidene Fluoride (PVDF), the sieves are welded to one side of the body, then the packing material is inserted and finally the second sieve is placed and hot welded. Polyvinylidene Fluoride is a relatively low cost fluoropolymer that is injection mouldable easily because of its low melting point (around 177° C.), quite strong and resistant to solvents acids and bases.

Prior to carrying out SPE, the cartridge is temporarily clamped between two jaws of a clamp so that passages in the jaws are connected in series with the passage through the cartridge body so as to form a continuous fluid path. Fluid can then be pumped through the cartridge to initiate interaction between components in the fluid and the packing material in the form of SPE.

A problem associated to existing SPE cartridges is insufficient resistance to pressures higher than 25 MPa. Such cartridges are unsuitable for online communication with UHPLC, because UHPLC involves the application of higher pressures (sometimes up to 120 MPa). UHPLC is becoming increasingly important for the analysis of complex samples because of its high separation power.

Another problem of existing SPE cartridges is insufficient resistance to traditional HPLC pressures at temperatures higher than around 70° C. This very much restricts the use of "Temperature Assisted Solid Phase Extraction" (TASPE), see for instance applicant's European patent 1 159 597.

More in general, the use of conventional cartridges at high pressures entails leakage problems where surfaces of the jaws and of the SPE cartridge are pressed against each other.

SUMMARY OF THE INVENTION

It is an object of the present invention to provide a cartridge for selecting an analyte online with HPLC, with an improved resistance against leakage at high temperature and/or pressure.

According to the invention, this object is achieved by providing a cartridge for solid phase extraction of an analyte from a liquid, comprising a cartridge body bounding a passage for retaining a sorbent, the passage extending from a first end face to a second end face opposite the first end face of the cartridge body, the first and second end faces facing in diametrically opposite directions. The cartridge body comprises a core of a first material extending around the passage and sealing rings of a second material, extending around an axis of the passage, at the first and second end faces, surface portions of the sealing rings constituting surface portions of the first and second end faces. The first material is stronger and stiffer than the second material.

The invention can also be embodied in a kit including such a cartridge and a cartridge clamp comprising a pair of clamping jaws having clamping faces opposite of each other and facing each other, conduits extending through the jaws and having mutually aligned open ends constituting openings in the clamping faces for clamping the cartridge in-between with the passage aligned with the openings. At least one of the clamping faces has at least one ring-shaped protrusion or recession extending around an axis of the passage or of one of the conduits. The protrusion or recession is arranged for contacting and deforming one of the sealing rings contacted thereby when the cartridge is clamped between the jaw with the passage aligned with the openings in the clamping faces.

Furthermore, the invention can be embodied in a method of moulding a cartridge body for a cartridge for solid phase extraction of an analyte from a liquid, the cartridge body bounding a passage for retaining a sorbent, the passage extending from a first end face to a second end face, opposite the first end face of the cartridge body, the first and second end faces facing in diametrically opposite directions. A core of a first polymeric material extending around the passage is moulded, Sealing rings of a second polymeric material are insert moulded to the core. The sealing extends around ends of the passage at the first and second end faces. Surface portions of the sealing rings constitute surface portions of the first and second end faces. The first polymeric material is stronger and stiffer than the second polymeric material. The second polymeric material is injected into at least one ring shaped cavity between the core and a mould and flows from the ring shaped cavity to a cavity defining at least one the sealing rings via at least one channel in the core.

Particular elaborations and embodiments of the invention are set forth in the dependent claims.

Further features, effects and details of the invention appear from the detailed description and the drawings.

DETAILED DESCRIPTION

Figure 1:
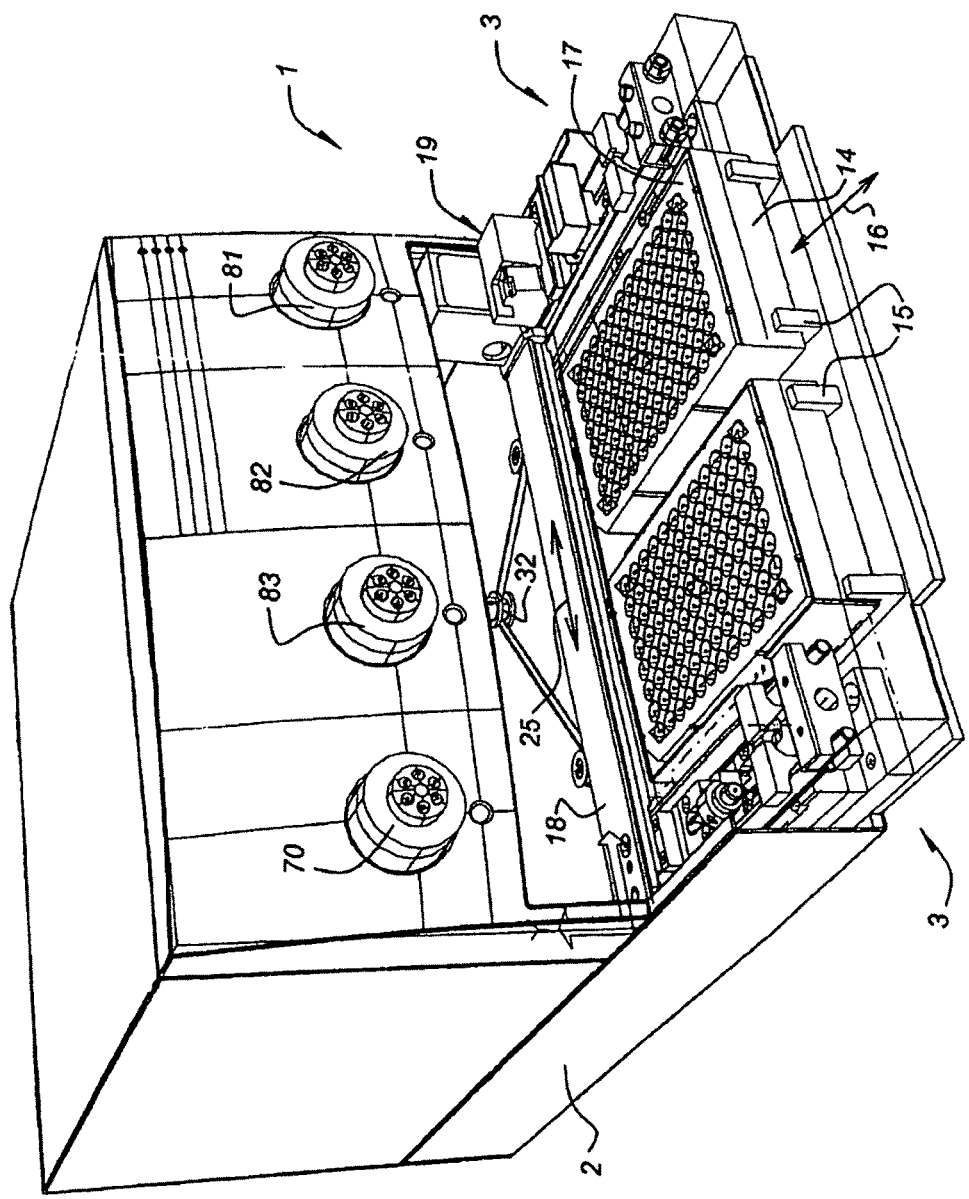
FIG. 1 is a perspective view representation of an example of an SPE instrument.
Figure 2:
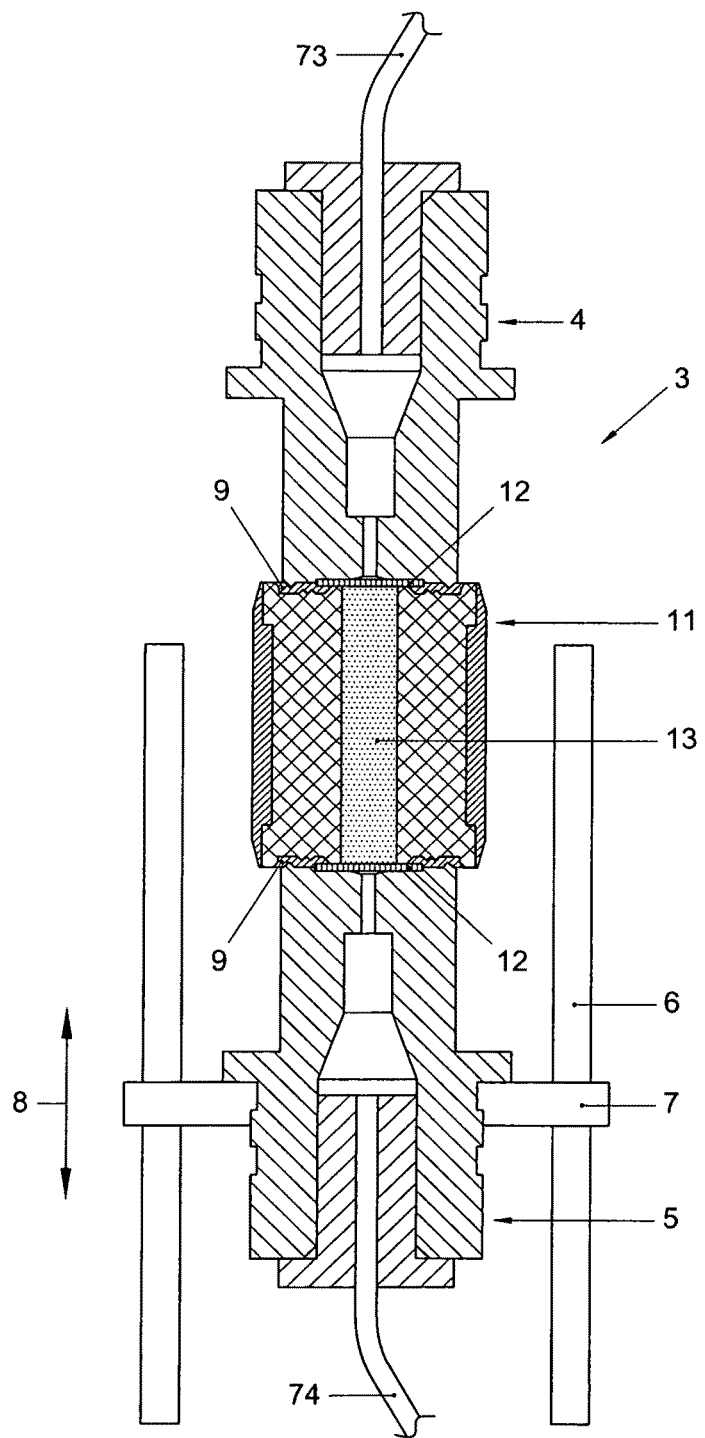
FIG. 2 is a diagrammatic top plan view of a cartridge holder of the apparatus shown in FIG. 1 containing an example of a cartridge according to the invention.

FIGS. 1-7 show an example of a solid phase extraction (SPE) instrument 1 with cartridges according to the present invention. The SPE instrument has a housing 2 and a cartridge holder 3 on the left and right-hand side of the open front of the housing 2. As is best seen in FIG. 2, each of these cartridge holders 3 has two clamping jaws 4 and 5, of which a first clamping jaw 4 is fixed relative to the housing (at least during operation) and a second clamping jaw 5 is mounted to a slide 7 movable along guides 6. The slide 7 is movable to and fro along the guides 6 with the clamping jaw 5 as indicated by a double arrow 8. A conduit 73 is connected to clamping jaw 4 and a conduit 74 is connected to clamping jaw 5. The conduits 73 and 74 extend through the clamping jaws 4 and 5 and have end apertures in frontal clamping faces 91 (see FIG. 9) of the clamping jaws 4 and 5, which frontal faces 91 face each other.

When the clamping jaws 4 and 5 have been moved apart, a cartridge 11 can be placed between the jaws 4, 5, after which clamping jaw 5 can be moved towards clamping jaw 4 in order to clamp the cartridge 11 between the clamping jaws 4 and 5. When a cartridge 11 is clamped between the clamping jaws 4, 5, sharp, circular ribs 93 constituting elevations on the clamping faces 91 of the clamping jaws 4, 5 are pressed into end faces of the cartridge 11, sealing end faces of the cartridge 11 against the jaws 4, 5.

The jaws 4, 5 can be released from the cartridge 11 to allow the cartridge to be removed from between the jaws 4, 5.

According to the present example, the cartridge 11 is an essentially cylindrical body through which a channel 13 extends in axial direction of the cartridge 11 from a first end face to a second, opposite end face of the cartridge. Two sealing membranes 12 at opposite ends of the channel retain a sorbent in-between. When the cartridge 11 is clamped between the jaws 4, 5, the conduits 73, 74 are in communication with the channel 13 so that a liquid can be supplied via the conduit 73, passed through the cartridge 11 and discharged via the conduit 74, or conversely, supplied via the conduit 74, passed through the cartridge 11 and discharged via the conduit 73.

The cartridge 11 may for instance have an outer diameter of 5-15 mm and a length of 5-20 mm, the channel 13 through the cartridge 11 may for instance have an internal diameter of 0.5-4 mm. The SPE instrument according to the present example is suitable for operating with cartridges of different length without modification.

Two cartridge magazine holders 14, which are movable to and fro in accordance with double-headed arrow 16, guided by magazine holder guides 15, can also be seen in the exposed section of the SPE instrument 1 and at the front. Each cartridge magazine holder 14 is provided with a cartridge magazine 17 containing 96 cartridges 11 arranged in an 8×12 matrix configuration.

Figure 3:
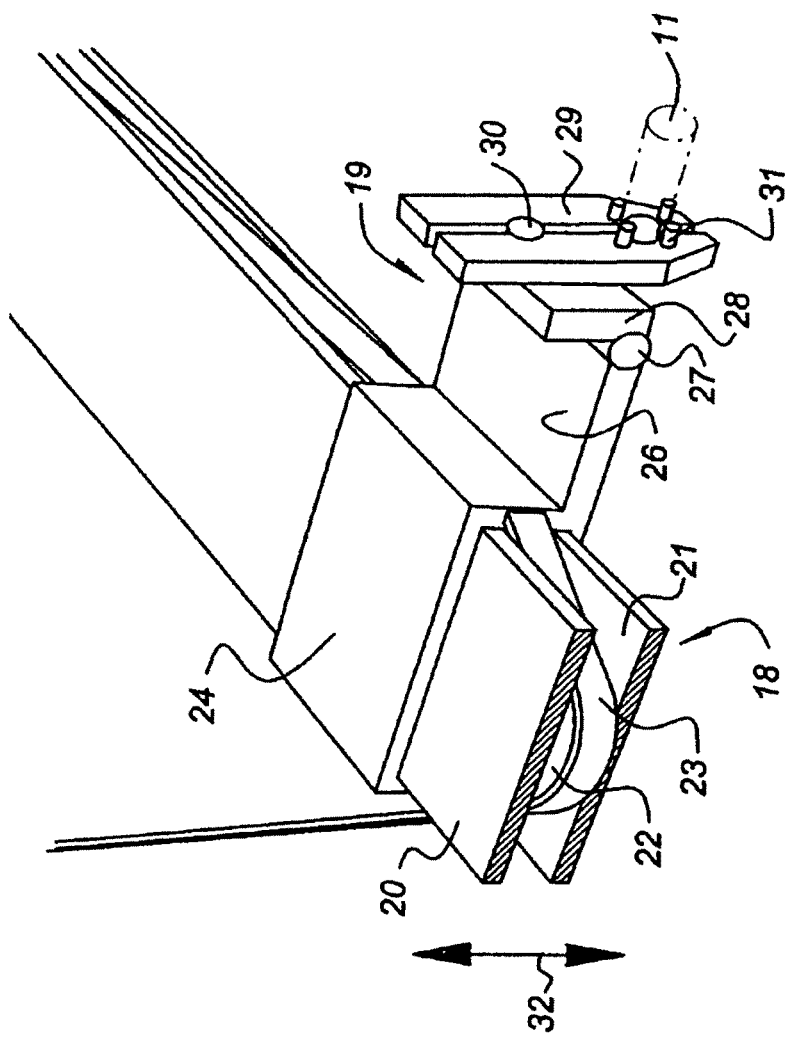
FIG. 3 is a diagrammatic, perspective view of part of a guide bridge, provided with a cartridge gripper, of the SPE instrument shown in FIG. 1.

A guide bridge 18 carries a cartridge gripper 19 (FIG. 3). The guide bridge 18 has an upper guide bar 20 and a lower guide bar 21. A guide wheel 22 is arranged at each longitudinal end of the guide bridge 18 between the upper and lower guide bars 20, 21. A slide 24 is mounted to the guide bridge 18, which slide 24 is movable/displaceable to and fro along the guide bridge 18 as indicated by double-headed arrow 25 in the longitudinal direction of the guide bridge 18. A forward-facing arm 26 of the slide 24 carries a support arm 28 hinged to its free end by means of hinge 27. Two gripper arms 29, which can be swivelled apart and towards one another about a pivot structure 30, are arranged alongside each other and mounted to the support arm 28. The gripper arms 29 are each provided with two gripper elements 31 in the form of pins.

By means of the cartridge gripper 19 a desired cartridge 11 can be picked up from a specified cartridge location, for instance from any location from the 8×12 matrix pattern, transferred to the cartridge holder 3 and be placed in the cartridge holder 3. A cartridge 11 may also be removed from the cartridge holder 3 again and transferred to the cartridge magazine 17 and placed in any specified position in the cartridge magazine 17 or, optionally, in another cartridge magazine. It is also possible by means of the cartridge gripper 19 to transfer a cartridge from one cartridge location to another cartridge location or to take a cartridge from a cartridge holder 3 and place it in another cartridge holder 3 or in a waste container.

The SPE instrument is provided with a control system that is equipped to select one of the cartridge locations depending on a command given to the control system via input means and to control the transport system to place a cartridge in that specific cartridge location or to remove a cartridge from that specific cartridge location. This control system can include a program which can be executed in a data processing unit of the SPE instrument or can be executed by a separate computer, such as a so-called personal computer connected to the SPE instrument. The input means can include manual input means, automated input means, such as an input program controlled by a computer or a combination of the two.

As soon as the control system has selected a specific cartridge location in a specific cartridge magazine, the control system is able to control drives for displacing the bridge 18 and drives for displacing the cartridge gripper slide 24 along the bridge 18 such that the cartridge gripper 19 is positioned with its gripper elements 31 around the cartridge in the selected position and to grasp this cartridge.

The slide 24 is movable into the correct position on the guide bridge 18 by a toothed belt 23 attached thereto and a toothed belt drive 33. To position the gripper elements 31 in a vertical position the support arm 28 can be swivelled into a horizontal position by means of swivelling means (not shown) such as, for example, a piston-cylinder unit having one end coupled to the support arm 28 and the other end coupled to the slide 24. The guide bridge 18 can also be moved up and down in vertical direction in accordance with double-headed arrow 32 by means of lifting means (not shown) such as, for example, a cylinder piston unit, in order to be able to grasp a cartridge and to be able to lift a cartridge that has been grasped out of its cartridge location in the cartridge magazine. It will be clear that the control system is also capable of controlling all these movements in the reverse direction to position a cartridge in a selected position. Instead of moving the guide bridge 18 up and down as indicated by double headed arrow 32, it is also conceivable to move the support arm up and down with respect to the guide bridge in accordance with the double-headed arrow 32 or to swivel the support arm towards a cartridge in order to grasp said cartridge and to swivel it away from the cartridge magazine in order to lift a cartridge from a cartridge location (or the other way round in the case of placing a cartridge in a cartridge magazine).

The control system is thus capable, depending on a command given to the control system via input means, of determining a cartridge location containing a cartridge suitable for the SPE process to be carried out and to have this cartridge placed in a cartridge holder for carrying out the SPE process. Data regarding the order in which the cartridges are used in an SPE process and the progress, i.e. which cartridges have been used, are stored in a memory.

If each cartridge location in each cartridge magazine contains a predetermined cartridge, these data then have to be entered in the control system. However, it is also conceivable to link a coding or data carrier with each cartridge magazine, which coding or data carrier contains information on which type of cartridge has been placed in which cartridge location. These data can then be input into the control system, optionally automatically, when placing a cartridge magazine in the cartridge magazine holder.

Conceivable codings and data carriers are, for example, RF (radio frequency) codings, bar codes, dot codes, radiographically readable memory chips, etc.

With regard to the cartridge holder 3 it must also be pointed out that the clamping head, or at least the movable clamping head 5, will also be controllable by the control system. As will be clear from FIG. 1 and FIG. 2, the cartridge, which has been taken out of the cartridge magazine in the vertical position, is first brought into a horizontal position and then placed with an end face in contact with the fixed clamping head 4. The clamping head 5 is then moved towards the clamping head 4 by a linear drive unit (not shown) for instance a piston-cylinder unit or a screw drive.

As is shown in FIGS. 4-7, the SPE instrument according to the present example further includes a solvent feed device 40 and a sample feed device 41. The block indicated by 1 in FIGS. 4-7 corresponds to the SPE instrument in FIG. 1.

The SPE instrument according to the present example further has a system of lines (conduits) and valves which can be controlled by the control system and via which a wide variety of liquid communications can be obtained. Some examples of liquid communications that can be obtained will be described below.

The solvent feed device 40 has an injection pump 44, also termed a syringe pump, which is provided with a pressure sensor 48 which is capable of measuring the liquid pressure in the injection pump, or the line system connected to the latter, during suction and/or delivery by the injection pump 44. The pressure sensor 48 is also connected to the control system for outputting a signal representing the measured pressure to the control system. The injection pump 44 has a piston housing 45 in which a piston 46 is accommodated. Movement of the piston 46 can be controlled by a linear drive unit (not shown) under control of the control system. The injection pump 44 is connected for drawing in or expelling liquid via the compressed suction/delivery line 47. The pressure sensor 48 is fitted in order to measure the pressure in the suction/delivery line 47. The suction/delivery line 47 opens into a port of a multi-port valve 49. Four other ports 51, 52, 53 and 54, are solvent feed lines, port 50 is a discharge port for waste, and solvent can be passed to the sample feed device 41 via port 55 when the line system of the SPE instrument is under pressure. In the embodiment according to FIG. 4, the multi-port valve 49 is of the type that is suitable for switching under high pressure. This makes this multi-port valve 49 less suitable for rapid switching between the one solvent connection and the other solvent connection. In order to nevertheless be able to switch rapidly and reliably between different solvent feeds while drawing solvent into the injection pump 44, solvent connection 54 is connected to one side of a second multi-port valve 56, which on its other side is provided with six solvent connection ports A to F. Operated by means of a solenoid, this second multi-port valve 56 can switch rapidly from the one solvent connection to the other solvent connection, so that a mixture of different solvents can be drawn in during a suction stroke.

Both the second multi-port valve 56 with six solvent connections 57 and the first multi-port valve 49 are switchable under control of the control system, preferably independently of one another. The control system is further equipped to be able to control the speed at which the piston 46 is moved in the delivery direction or the suction direction and/or to be able to control this in such a way that a specific pressure level is maintained or followed in the suction/delivery line or internal injection pump 44 and/or that a specific volume of solvent or solvents is drawn into the injection pump 44 or is delivered into the line system by means of the injection pump 44.

The sample feed device 41 is equipped with an injection pump 60, which operates in a manner similar to the operation of the injection pump 44, and is also operable under control of the control system. Via line 62, line 66, coil 67, line 68 and line 63, sample liquid can be drawn in from sample containers 65 until at least line 68 and coil 67, and preferably also line 66, have been filled with sample liquid while multi-port valve 64 is in the switch position shown in FIG. 4.

In the schematic representation of the multi-port valves 64, 70, 81, 82 and 83 in FIGS. 4-7, the black areas between neighbouring ports represent open liquid communications between neighbouring connection ports. The white spaces between ports represent closures between neighbouring ports. The multi-port valves 64, 70, 81, 82 and 83 are switchable between two positions. On switching between the two positions, the ring of black and white sections is, as it were, turned through 60°, causing each port to be connected with the other one of its circumferentially neighbouring ports and disconnected from its previously connected circumferentially neighbouring port.

Figure 4:
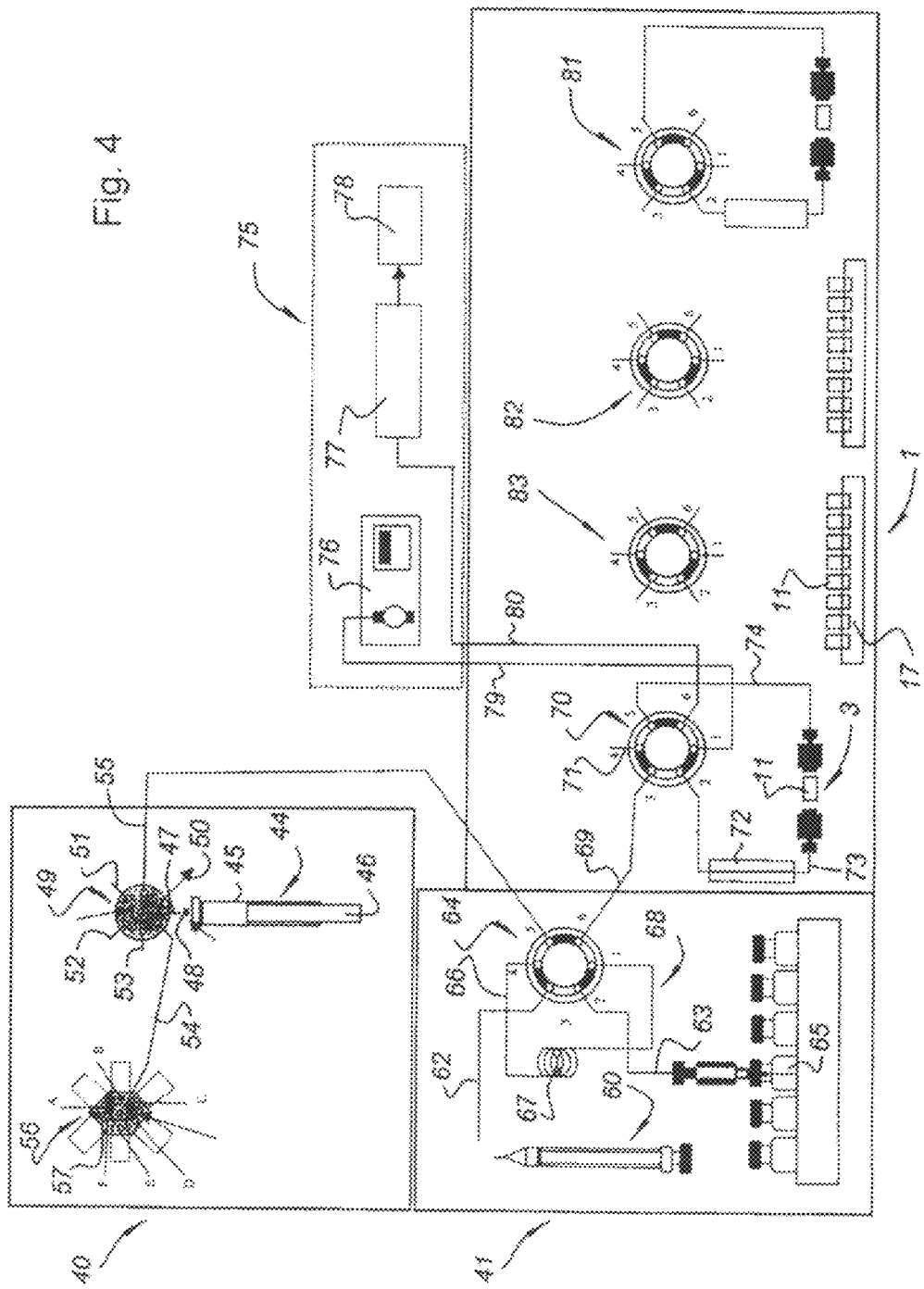
FIG. 4 is a diagrammatic frontal view of the SPE instrument according to FIG. 1 and of a solvent feed device and a sample feed device connected thereto.

When multi-port valve 64 is in the switch position shown in FIG. 4, it is possible to simultaneously fill the sub-line system of the sample feed device 41 with a sample liquid and feed solvent via line 55, multi-port valve 64 and line 69, to multi-port valve 70. As far as the operating positions are concerned, multi way valve 70 is similar to multi-port valve 64. When multi-port valve 70 is in the switch position shown, solvent supplied via line 69 will be discharged via line 71.

However, when multi-port valve 70 is switched over, solvent supplied via line 69, or optionally sample liquid supplied via line 69, will be fed via line 72 and optional heating/cooling means 73 to the cartridge holder 3, passed through the cartridge 11, returned to the multi-port valve 70 via line 74 and discharged via line 71.

In addition to the SPE instrument 1, a so-called HPLC analytical instrument 75 is shown diagrammatically in dotted lines. This HPLC analytical instrument 75 has a HPLC pump 76, a column 77 and a detection device 78 connected downstream of the column 77. The HPLC pump 76 is connected via a line 79 to the multi-port valve 70 and the column 77 is connected via a line 80 to the multi-port valve 70. With the multi-port valve 70 in the operating position shown in FIG. 4, the HPLC pump 76 can pump liquid through, successively, the line 79, the valve 71, the line 72, the heating/cooling heat exchanger 73, the line, the cartridge 11, the line 74, the valve 70, the line 80, the column 77 and the detection device 78.

In an apparatus as shown in FIGS. 4-7, an SPE process can for instance be carried out in the following manner:
 A. Conditioning a sorbent in the channel 13 extending through the cartridge 11 for a subsequent application of sample liquid.
 B. Conditioning usually includes wetting and an equilibrating;
 C. Loading a sample of liquid into the system.
 D. Passing the sample of the liquid through the sorbent.
 E. Washing the sorbent, after it has been exposed to the sample liquid, to flush undesired substance from the sorbent.
 F. Eluting the analyte taken up in the sorbent from the sorbent in order to be able to subject this analyte to a further treatment.

Figure 5:
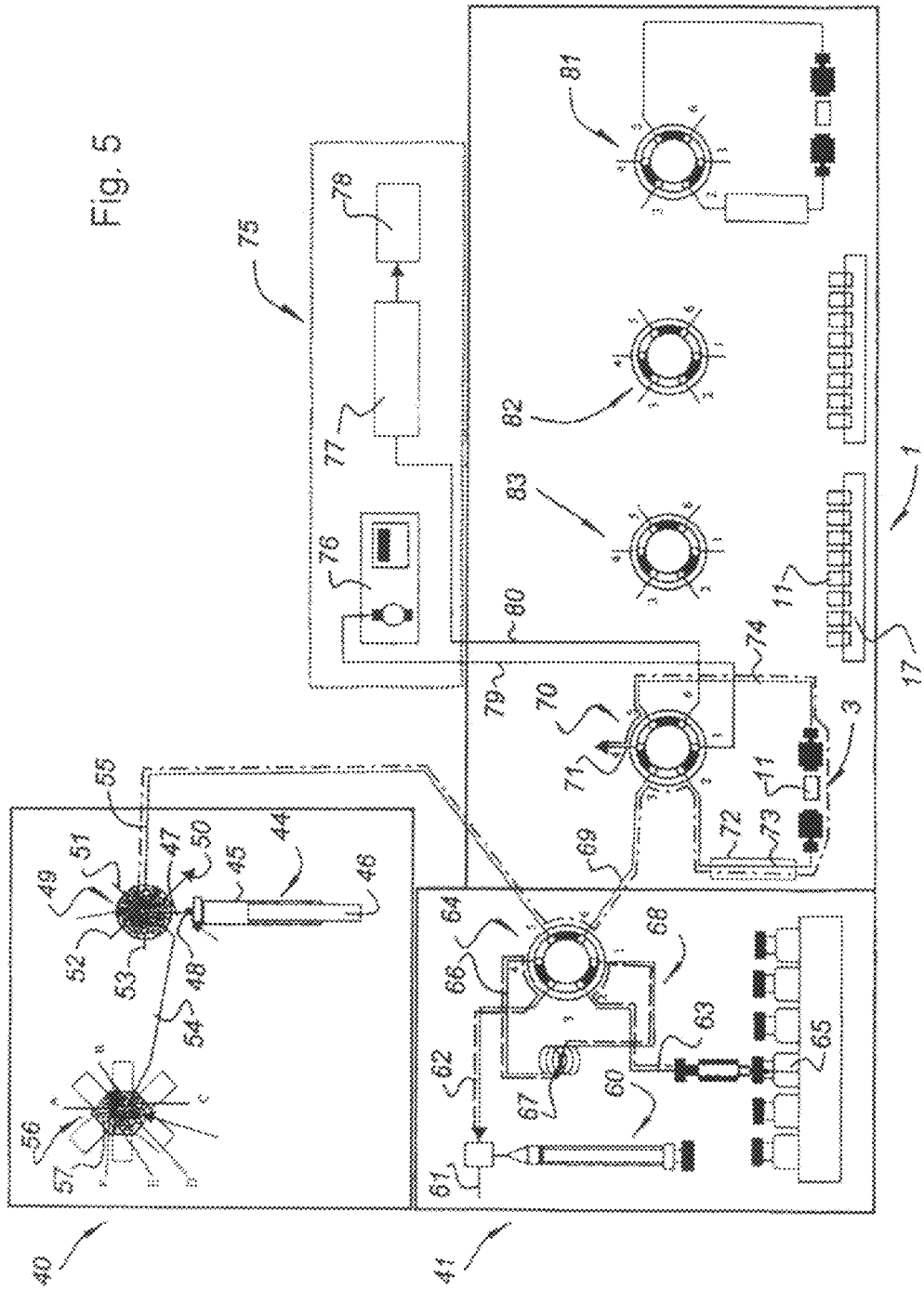
FIGS. 5-7 are diagrammatic frontal views of the set-up according to FIG. 4 in different operating positions.

FIG. 5 shows the switch positions for the multi-port valves 64 and 70 during the stages A and B. Stage A is illustrated in more detail by indicating the stream of solvent through the line system by a dash-and-dot line pattern running parallel to the part of the line system through which the solvent flows.

Loading of a sample of liquid into the sub-line system of the sample feed device 41 is illustrated by a dotted line pattern along the parts of the sub-line system through which sample liquid flows. During the conditioning of the sorbent, for example, solvent supplied via port 52 and solvent supplied via port 53 are passed through cartridge 11. Moreover, by drawing in solvent via multi-port valve 56 during the suction phase of the injection pump 44 and switching multi-port valve 56 while drawing in, a mixture of solvents can be collected in injection pump 44, after which this mixture can be passed through the sorbent in the cartridge 11 during the delivery phase.

Figure 6:
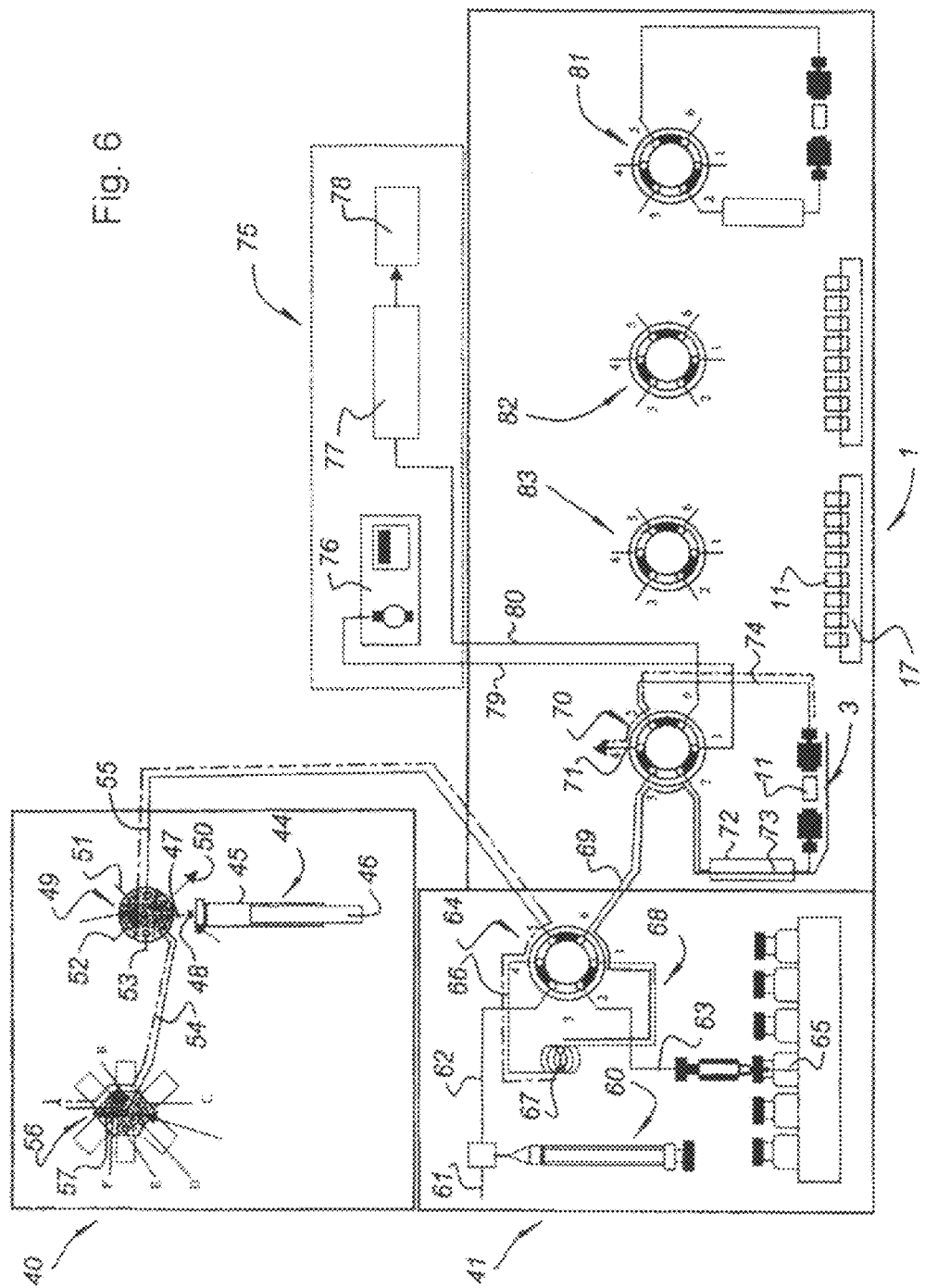

In FIG. 6, the switch positions for the valves 64 and 70 during stages C and D are shown. The sample liquid (dotted line) is driven through the sorbent in the cartridge 11 by means of a wash solvent (dash-and-dot line) while a residual volume of conditioning sorbent (broken line) is driven out of the system.

Figure 7:
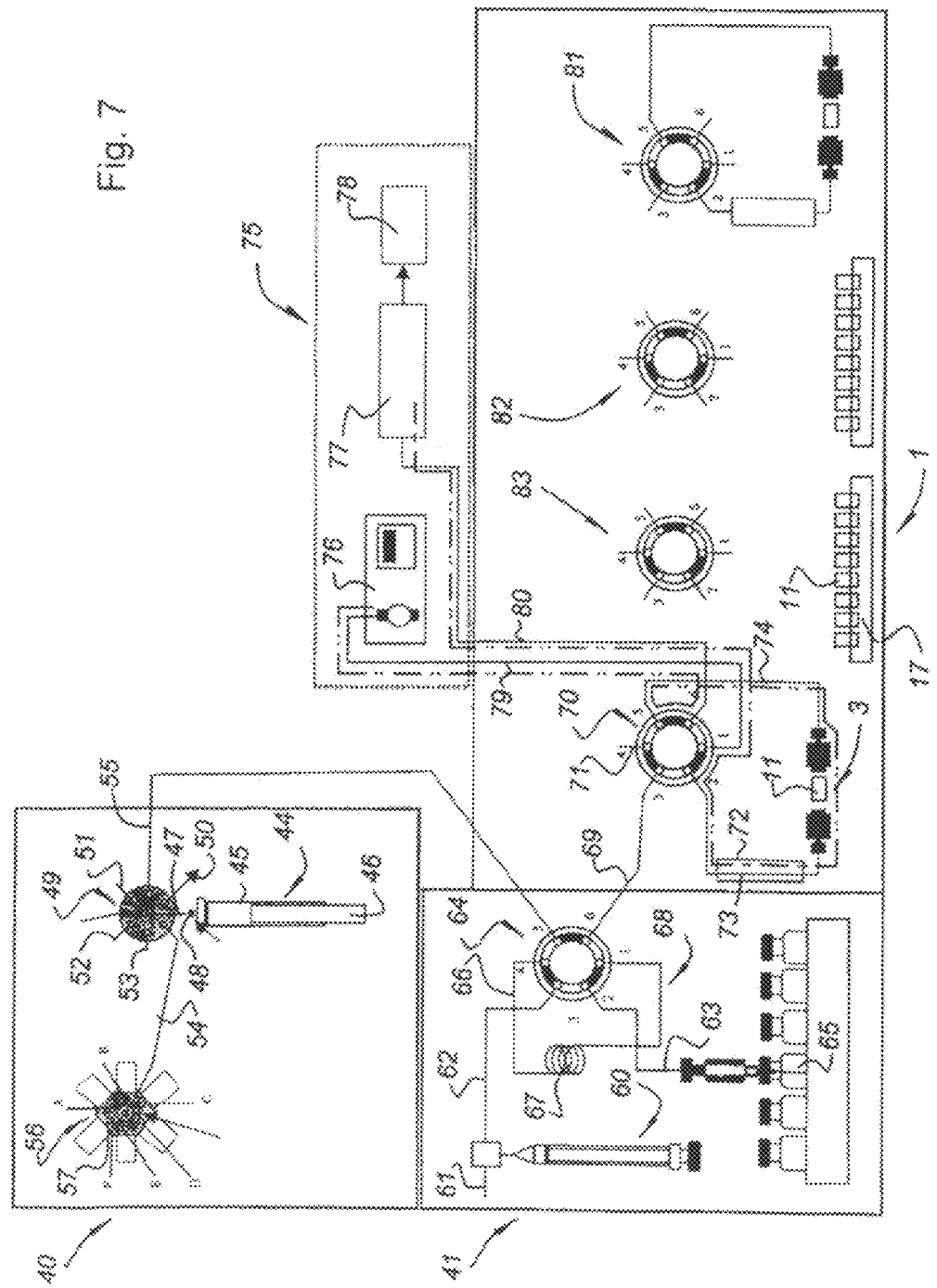

FIG. 7 then shows switch positions for the valves 64 and 70 during stage E. The pump 76 of the HPLC instrument pumps the elution liquid (indicated by a dash-and-double-dot line) from the pump 76 through the line system, through the sorbent in the cartridge 11 and through the column 77.

As is disclosed in more detail in European patent 1 159 597, the HPLC analytical instrument may also be connected to an additional multi-port valve 81, to which a second cartridge holder is connected. Furthermore, if the multi-port valves 64, 70, 81, 82 and 83 are suitably actuated, the first solvent feed device 40 can feed solvent both through the left-hand and through the right-hand cartridge holder 3 and the sample liquid can also be fed through both the right-hand and the left-hand cartridge holder 3. It is also possible to connect a gas source to the multi-port valve 83, and to connect multi-port valve 81 to an analytical instrument such as a gas chromatograph.

During the elution stage, the cartridge 11 is exposed to essentially the full pressure at which the eluent is pressed through the HPLC column. The pressure applied is often higher than 25 MPa and during UHPLC even higher pressures, sometimes up to 120 MPa occur. UHPLC is becoming increasingly important for the analysis of complex samples because of its high separation power.

Furthermore, if "Temperature Assisted Solid Phase Extraction" (TASPE) is applied, liquid is heated up, in the present example by heater 72, before it reaches the cartridge 11 to enhance elution. This causes the cartridge 11 to be heated up as well, for instance to temperatures higher than around 70° C. At such elevated temperatures leakage of cartridges occurs even at conventional HPLC pressures, in particular if the cartridge is loaded with pressure for a relatively long time.

In FIGS. 2 and 8-12 an example of a cartridge according to the invention which, when clamped, provides an improved resistance against leakage at high pressures and/or liquid temperatures is shown.

The cartridge 11 has a cartridge body 84 bounding the passage 13 for retaining a sorbent. In the present example, the sorbent is positioned in the passage 13 and represented by a dotted shading. The cartridge 11 includes sieves 12 at end faces 85, 86 of the cartridge 11 to retain the sorbent in the passage 13. It is, however, also possible to provide a cartridge without sorbent in the passage 13 and or with no sieves or with one or both sieves mountable to the cartridge, for instance after a sorbent has been introduced into the passage.

The passage 13 extends from the first end face 85 to a second end face 86, opposite the first end face 85 of the cartridge body 84. The first and second end faces 85, 86 face in diametrically opposite directions.

The cartridge body 84 has a core 87 of a first material extending around the passage 13 and sealing rings 88 of a second material, extending around ends of the passage 13 at the first and second end faces 85, 86. Surface portions 89 of the sealing rings 88 constituting surface portions of the first and second end faces 85, 86. In the present example, the first material and the second material are polymeric materials. However, the first and/or the second material may in principle also be or include other types of materials. For instance, the first and second materials could metals or composite materials, such as fiber reinforced resin.

In the present example, the core directly bounds the passage 13, but the passage 13 may also be bound by the second polymer material or yet another material.

The first polymeric material of the core 87 is stronger and stiffer than the second polymeric material.

The provision of a core around the passage of a stiffer material provides a substantially improved resistance against leaking. Preferably, overall dimensions of the cartridge are not increased to maintain compatibility with existing cartridge handling systems. Preferably the dimensioning and material of the core are such that pressures of up to at least 100 MPa at room temperature and pressures of up to at least 25 MPa at liquid temperatures up to 100° C. can be resisted without leakage between the clamping faces 91 and the cartridge or between the sieve and the cartridge body. To enhance resistance against leakage, clamping forces are preferably increased. The core around the passage also contributes to an increased axial compression strength of the cartridge, which allows to apply such an increased axial clamping pressure. The clamping pressure may for instance be increased to at least 1600 N and more preferably to at least 1900 N. A maximum clamping pressure may for instance be 2500 N.

Because the second polymeric material of the sealing rings is more flexible than the first polymeric material, a hermetic seal between the clamping faces 91 of the jaws 4, 5 and the end faces of the cartridge is reliably obtained.

The sealing rings 88 are each embedded in a ring-shaped recess 90 (see FIGS. 11 and 12) in the core 87. The recesses 90 each extend around an end of the passage 13 at one of the first and second end faces 85, 86. Because the sealing rings are each embedded in a recess, creep of the second polymeric material of the sealing rings and accordingly relaxation of the contact pressure between the sealing rings and the clamping surfaces is counteracted. In the present example a closed ring is formed both inside and outside the sealing rings. This traps the second polymeric material when pressure is applied by the clamping face 91.

This allows to apply clamping pressures that are higher than the pressure the second polymeric material can withstand (at least at operating temperature), so that the second polymeric material accommodates to the clamping surfaces while flowing away of the material of the second polymeric material, even at elevated temperatures is counteracted sufficiently to maintain reliable sealings between the clamping surfaces and the cartridge.

Figure 9:
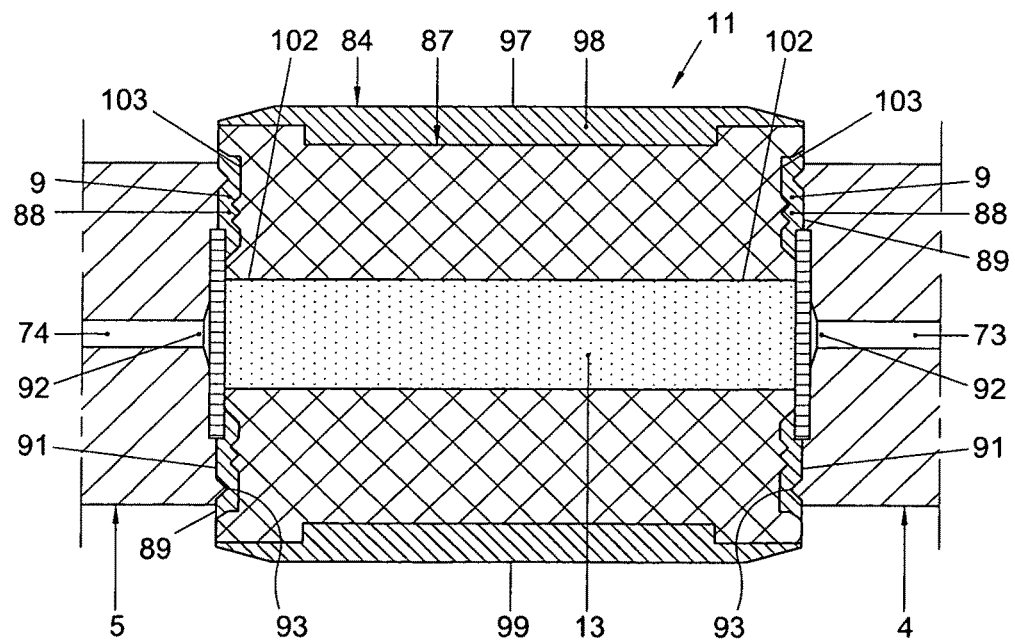
FIG. 9 is a side view in cross-section of the cartridge shown in FIGS. 2 and 8 in clamped condition.
Figure 10:
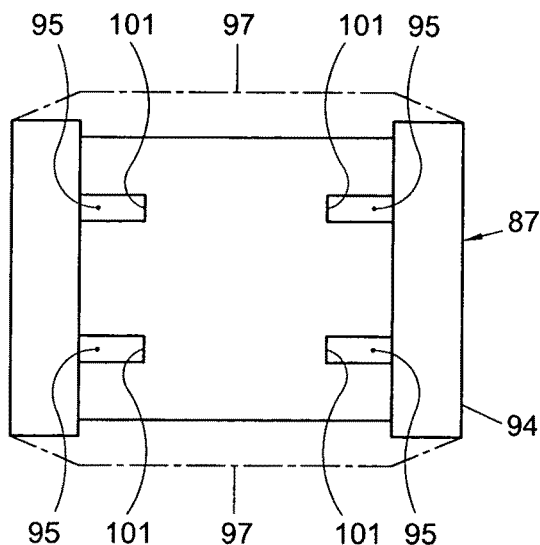
FIG. 10 is a side view of a core member of the cartridge shown in FIGS. 2, 8 and 9.

As is shown in FIG. 9, the clamping jaws 4, 5 have clamping faces 91 opposite of each other and facing each other. The conduits 73, 74 extend through the jaws 4, 5 and have mutually aligned open ends 92 constituting openings in the clamping faces 91 for clamping the cartridge in-between with the passage 13 aligned with open ends 92 of the conduits 73, 74 through the jaws 4, 5. The clamping faces 91 each have a ring-shaped protrusion 93 each extending around an axis of one of the conduits 73, 74. The protrusions 93 are arranged for each contacting and deforming one of the sealing rings 88 when the cartridge 11 is clamped between the clamping jaws 4, 5 with the passage 13 aligned with the openings 92 in the clamping faces 91.

Figure 8:
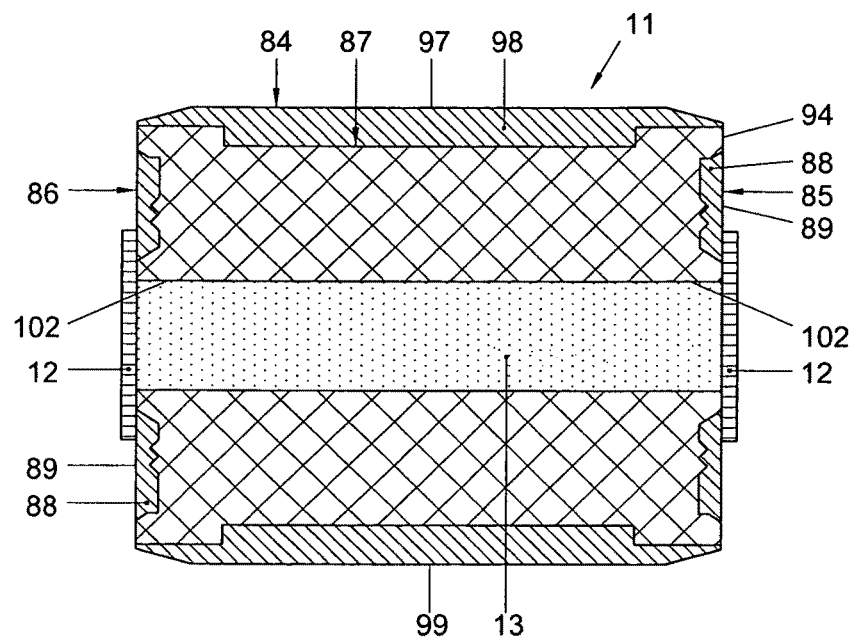
FIG. 8 is a side view in cross-section of the cartridge shown in FIG. 2.

As is best seen when comparing FIGS. 8 and 9, the protrusions 93 locally deform the sealing rings 88 when the cartridge 11 is clamped between the clamping jaws 4, 5. Thus, in a ring-shaped zone around the passage 13, a locally increased clamping force is generated and the material of the sealing rings 88 is particularly effectively forced to accommodate to the shape of the clamping faces 91. Also, the protrusions 93 provide grip on the material of the sealing rings 88, so that outward creeping of the material of the sealing rings 88 is counteracted. Thus a particularly effective sealing is obtained. It is observed that a similar effect could also be obtained by providing the clamping faces with ring-shaped recesses each extending around an axis of one of the conduits into which recessed portions of the sealing rings, such as co-axial ring-shaped protrusions on the sealing rings, are pressed when the cartridge is clamped between the jaws.

For obtaining a high pressure liquid tight sealing, it is furthermore advantageous that the ring-shaped protrusions 93 are each radially spaced from outer and inner contours of the respective sealing ring 88 when the cartridge 11 is clamped between the clamping jaws 4, 5 with the passage 13 aligned with the openings 92 in the clamping faces 91.

Figure 11:
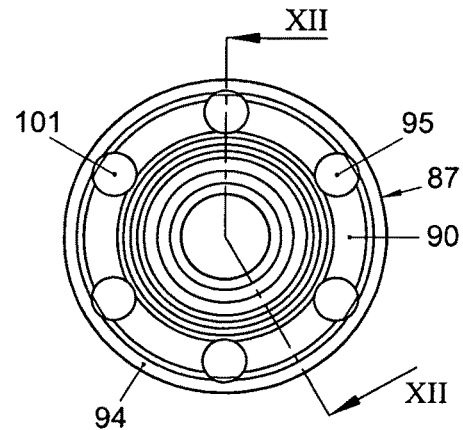
FIG. 11 is a frontal view of the core member shown in FIG. 10.
Figure 12:
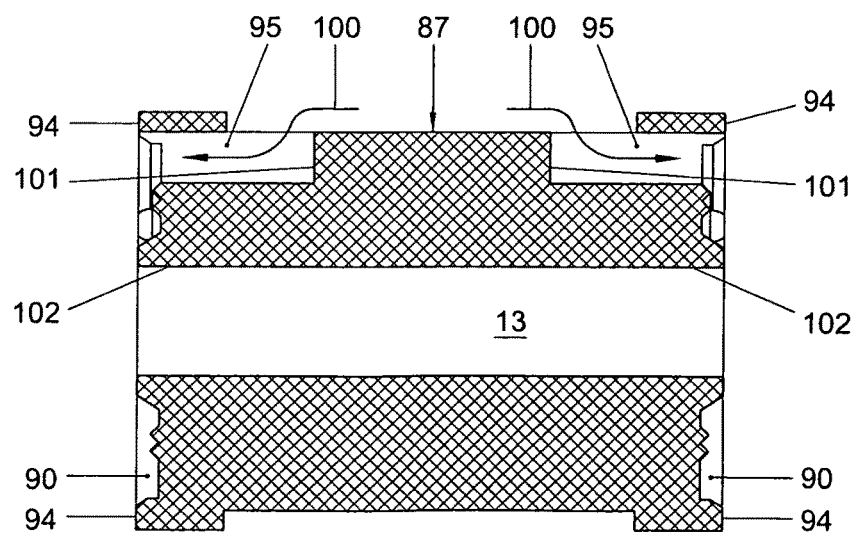
FIG. 12 is a cross-sectional view along the lines XII-XII in FIG. 11.

The cartridge 11 is preferably made moulding the core 87, for instance by injection moulding and by subsequently insert moulding the sealing rings 88 to the core 87 by injecting the second polymeric material into at least one ring shaped cavity between the core 87 and a mould and causing the second polymeric material to flow from the ring shaped cavity to a cavity defining at least one of the sealing rings 88 via at least one channel 95 in the core 87. In FIG. 11, only one of the channels 95 is designated by a reference number. In the present example, the ring shaped cavity is bounded by a ring shaped recess 96 in the circumference of the core 87 and an inner wall of the mould complementary to the circumferential surface 97 of the cartridge 11 as shown in FIGS. 2, 8 and 9 and as indicated by dash-and-dot lines in FIG. 10.

End surfaces 94 of the core 87 each constitute a surface portion of one of the end faces 85, 86 of the cartridge. The end faces directly contacting inner surface portion of the mould accurately maintain the axial position of the core 87 in the mould prior to and during injection of the second polymeric material. The radial position of the core 87 may be maintained by a mandrel accurately fitting in the passage 13 and extending through the mould into which the second polymeric material is injected.

After insert moulding, a circumferential ring or sleeve 98 of the second polymeric material around the passage 13 and the core 87 is obtained. The circumferential ring 98 has an an outer surface 97 constituting at least a portion of a circumferential surface of the cartridge body and a sprue mark 99 on said circumferential surface 97. The circumferential ring or sleeve 98 communicates with the sealing rings 88 via the channels 95 in the core 87. By insert moulding via a circumferential ring-shaped cavity, the second polymeric material is injected into the cavities defining the sealing rings 88 from inside the core, so the injection moulding sprue mark is obtained at the circumferential surface of the cartridge where relatively wide tolerances on shape and dimensions can be accepted without impairing functionality of the cartridge. Conversely, material flows into the cavities defining the sealing rings as indicated by arrows 100 in FIG. 12 without leaving a sprue mark on the sealing rings 88.

In the present example, both rings 88 are connected to the same circumferential ring 98. Since the sealing rings 88 constitute a single member, the second polymeric material can be injected via a single port. It is however also possible to provide that two circumferential rings are each connected to one of the sealing rings.

As is best seen in FIG. 11, the six channels 95 are circumferentially distributed. Via a plurality of channels evenly distributed in circumferential sense, the second polymeric material can flow into the cavities defining the sealing rings in a mainly axial direction and with relatively little flow in circumferential sense through the cavities defining the sealing rings is necessary. Thus, relatively short flow paths are obtained and a relatively uniform shrink of the material constituting the sealing rings during cooling is obtained even at relatively low mould temperatures. In turn, this is advantageous for achieving an effective sealing against the clamping faces of the jaws. Moreover, effective merging where flow paths meet is achieved, even at relatively low mould temperatures.

Furthermore, the second polymeric material in the channels also constitutes an effective anchoring of the sealing rings. Also for this purpose it is advantageous that the channels are circumferentially distributed. The number of channels may be lower than six, for instance three, four or five. While a higher number of evenly distributed channels is advantageous for a relatively uniform supply of the second polymeric material during injection moulding and an evenly distributed anchoring of the sealing rings, the complexity of the mould increases with the number of channels.

The channels each have an internal surface 101 (see FIGS. 10-12, in FIG. 11, only one of these surfaces is designated by a reference number) facing in axial direction towards a nearest end of the cartridge 11. These surfaces 101 provide axial support to the sealing rings 88 in the area of the channels 95 via the second polymeric material in the channels 95.

The core 87 has conical, ring-shaped end portions 102, each directly adjacent to an end of the passage 13 and extending around the passage 13. Each of the conical, ring-shaped end portions 102 projects in axial direction of the cartridge 11 to closely adjacent to the sieve 12 at the respective end of the cartridge 11. Outer surfaces of the sieves 12 constitute portions of the end surfaces 85, 86 of the cartridge 11, each directly abutting one of the clamping faces 91.

As is illustrated by FIGS. 8 and 9, in clamped condition, the sieves 12 are pressed slightly into the respective end of the cartridge body 84.

The conical, ring-shaped end portions 102 of the core 87 limit the distance over which the sieves 12 are pressed into the cartridge body and cause the counter pressure exerted by the relatively easily deformable second polymeric material to be relatively high. Thus a ring shaped area is obtained where, on the one hand the second polymeric material contacts the sieves so that a hermetic sealing is obtained while, on the other hand, deformation of the second polymeric material is limited and a ring-shaped sealing area is obtained where a high contact pressure is exerted, so that even at very high pressures in the passage 13, no leakage between the second polymeric material and the sieves occurs.

For achieving good heat resistance, even during prolonged application of a high pressure in the passage 13, it is advantageous that the first polymeric material has a higher glass transition temperature and a higher melting point than the second polymeric material. The lower melting point of the second polymeric material is advantageous for easy injection moulding with short cycle times, high accuracy and avoiding deformation of the core 87 when the second polymeric material is injected.

To counteract creep when hot liquids are processed, the first polymeric material preferably has a glass transition temperature higher than 80° C. and more preferably higher than 100° C. The first polymeric material may for instance be or contain a substantial amount of PEEK or fiber reinforced PPS.

The second polymeric material is preferably a fluoropolymer, such as Nylon, PTFE, or PVDF (Polyvinylidene difluoride) in view of broad chemical compatibility. Hydrophilic PVDF membranes bind far less protein than nylon, nitrocellulose or PTFE membranes.

The sieves 12 are each welded to one of the sealing rings 88, taking advantage of the relatively low melting temperature and therefore suitability for welding of the second polymeric material.

Ring-shaped portions 103 of each of the sealing rings 88 are free from the clamping surface 91 of the jaw 4, 5 contacting the sealing ring 88 when the cartridge 11 is clamped between the clamping jaws 4, 5 with the passage 13 aligned with the openings 92 in the clamping faces 91. The free surfaces of the second polymeric material allow the second polymeric material of the sealing rings 88 to bulge slightly out of the recess 90 in response to deformation by the protrusions 93. This ensures full engagement of the protrusions 93 and a controlled distribution of applied pressure between the area of the sieves 12 and the area of the protrusions 93.

The skilled person will appreciate that within the framework of the present invention as defined by the claims, many other variants than the examples and alternatives described above are conceivable. For instance, while in the discussed examples, cartridges are mainly symmetric designs with mutually identical ends, one axial end of the cartridge and accordingly the clamping face of the jaw on that side could be of a different design than the other axial end of the cartridge and the jaw on that side of the cartridge.

Furthermore, use can also be made of a cartridge not containing any sorbent. Instead, the cartridge may for instance be packed with a filter material or be equipped with one or two or more closure membranes or other membranes, the cartridge then constituting a filter or screen. Such a cartridge without sorbent can for instance be positioned in series with a cartridge containing sorbent. It is also conceivable to use such a cartridge without sorbent as a filter or screen or as a sample container in order to feed an analyte-containing sample directly to a further analytical instrument, without employing any SPE process, the cartridge then effectively constituting a filter or a sample container. Material physically retained in the cartridge may also constitute a chemical filter material, such a substance for catching phospholipids from a sample to counteract ionization suppression in MS.

The invention claimed is:

1. A cartridge for solid phase extraction of an analyte from a liquid, comprising
    a cartridge body bounding a passage for retaining a sorbent,
    the passage extending from a first end face to a second end face opposite the first end face of the cartridge body, the first and second end faces facing in diametrically opposite directions,
    wherein the cartridge body comprises a core of a first material extending around the passage and sealing rings of a second material, extending around an axis of the passage, at the first and second end faces, surface portions of the sealing rings constituting surface portions of the first and second end faces,
    a circumferential ring or sleeve of the second material extending around the passage and the core, the circumferential ring or sleeve having an outer surface constituting at least a portion of a circumferential surface of the cartridge body and a sprue mark on said circumferential surface, the second material integrally connecting the circumferential ring or sleeve with at least one of the sealing rings via at least one channel in the core, and the first material is stronger and stiffer than the second material.

2. A cartridge according to claim 1, wherein at least one of the sealing rings is embedded in a ring-shaped recess in the core, the recess extending around an axis of the passage at one of the first and second end faces.

3. A cartridge according to claim 1, wherein end surfaces of the core each constitute a surface portion of one of the end faces of the cartridge.

4. A cartridge according to claim 1, wherein the sealing rings constitute a single, integrally moulded member.

5. A cartridge according to claim 1, further comprising a plurality of said channels wherein at least some of the plurality of channels each have an internal surface facing in axial direction towards a nearest end face of the cartridge.

6. A cartridge according to claim 1, wherein the core has at least one conical, ring-shaped end portion, directly adjacent to an end of the passage and extending around an axis of the passage, the conical, ring-shaped end portion projecting in axial direction of the cartridge to closely adjacent to either an end surface of the cartridge or to closely adjacent to a sieve of which an outer surface constitutes a portion of an end surface of the cartridge.

7. A cartridge according to claim 1, wherein the first and the second material include or are constituted by polymeric materials and the polymeric material of the first material has a higher glass transition temperature and a higher melting point than the polymeric material of the second material.

8. A cartridge according to claim 1, wherein the first material includes or is constituted by a polymeric material having a glass transition temperature higher than 80° C.

9. A cartridge according to claim 1, wherein the second material includes or is a fluoropolymer.

10. A cartridge according to claim 1, further comprising a sieve welded to at least one of the sealing rings.

11. A kit of parts comprising:
a cartridge for solid phase extraction of an analyte from a liquid, comprising
a cartridge body bounding a passage for retaining a sorbent, the passage extending from a first end face to a second end face opposite the first end face of the cartridge body, the first and second end faces facing in diametrically opposite directions,
wherein the cartridge body comprises a core of a first material extending around the passage and sealing rings of a second material, extending around an axis of the passage, at the first and second end faces, surface portions of the sealing rings constituting surface portions of the first and second end faces, and
a circumferential ring or sleeve of the second material extending around the passage and the core, the circumferential ring or sleeve having an outer surface constituting at least a portion of a circumferential surface of the cartridge body and a sprue mark on said circumferential surface,
the second material integrally connecting the circumferential ring or sleeve with at least one of the sealing rings via at least one channel in the core,
wherein the first material is stronger and stiffer than the second material, and a cartridge clamp comprising a pair of clamping jaws having clamping faces opposite of each other and facing each other, conduits extending through the jaws and having mutually aligned open ends constituting openings in the clamping faces for clamping the cartridge in-between with the passage aligned with the openings, wherein
at least one of the clamping faces has at least one ring-shaped protrusion or recession extending around an axis of the passage or of one of the conduits,
the protrusion or recession being arranged for contacting and deforming one of the sealing rings contacted thereby when the cartridge is clamped between the jaws with the passage aligned with the openings in the clamping faces.

12. A kit according to claim 11, wherein the core has at least one conical ring-shaped end portion extending around the passage, closely adjacent to one of the clamping faces or closely adjacent to a sieve directly abutting one of the clamping faces.

13. A kit according to claim 11, wherein the ring-shaped protrusion or recession is radially spaced from outer and inner contours of the sealing ring when the cartridge is clamped between the jaws with the passage aligned with the openings in the clamping faces.

14. A kit according to claim 11, wherein a ring-shaped portion of at least one of the sealing rings is free from the clamping surface contacting the sealing ring when the cartridge is clamped between the jaws with the passage aligned with the openings in the clamping faces.

15. A method of moulding the cartridge of claim 1 comprising:
moulding the core of the first polymeric material extending around the passage,
insert moulding the sealing rings of the second polymeric material to the core, the sealing extending around ends of the passage at the first and second end faces, surface portions of the sealing rings constituting surface portions of the first and second end faces,
wherein the second polymeric material is injected into at least one ring shaped cavity between the core and a mold, and
flows from the ring shaped cavity to a cavity defining at least one the sealing rings via at least one channel in the core.

* * * * *